United States Patent [19]

Auge et al.

[11] 4,102,906

[45] Jul. 25, 1978

[54] PROCESS FOR PREPARING α-AMINO-β'-NITROANTHRAQUINONES

[75] Inventors: Wolfgang Auge, Odenthal-Hahnenberg; Karl-Werner Thiem, Cologne; Rütger Neeff, Leverkusen, all of Germany

[73] Assignee: Bayer Aktiengesellschaft, Leverkusen, Germany

[21] Appl. No.: 684,412

[22] Filed: May 7, 1976

Related U.S. Application Data

[63] Continuation of Ser. No. 485,284, Jul. 2, 1974, abandoned.

[30] Foreign Application Priority Data

Jul. 10, 1973 [DE] Fed. Rep. of Germany ....... 2334991

[51] Int. Cl.$^2$ ............................................. C07C 97/24
[52] U.S. Cl. .................................................. 260/382
[58] Field of Search ........................................ 260/382

[56] References Cited

U.S. PATENT DOCUMENTS

| | | | |
|---|---|---|---|
| 3,933,866 | 1/1976 | Seha ..................... | 260/382 |
| 3,933,867 | 1/1976 | Thiem et al. ........... | 260/382 |
| 4,003,924 | 1/1977 | Auge et al. ............. | 260/382 |

OTHER PUBLICATIONS

Lubs, "The Chemistry of Synthetic Dyes and Pigments", A.C.S. Monograph, Hafner Publishing Co., N.Y. (1955), p. 361.

*Primary Examiner*—Paul F. Shaver
*Attorney, Agent, or Firm*—Burgess, Dinklage & Sprung

[57] ABSTRACT

α-Amino-β'-nitroanthraquinone is prepared by reacting α,β'-dinitroanthraquinone with ammonia in an ether, an aliphatic, a cycloaliphatic or an optionally alkyl-substituted aromatic hydrocarbon, water or a mixture of the foregoing.

11 Claims, No Drawings

PROCESS FOR PREPARING
α-AMINO-β'-NITROANTHRAQUINONES

This is a continuation of application Ser. No. 485,284, filed July 2, 1974 now abandoned.

BACKGROUND

This invention relates to the Preparation of α-amino-β'-nitroanthraquinone

According to German Offenlegungsschrift No. 2,211,411, α,β-diaminoanthraquinones are obtained by reacting α,β-dinitroanthraquinones with ammonia in acid amides.

SUMMARY

Surprisingly, it has now been found that α-amino-β'-nitroanthraquinones can be obtained in high yields by reacting α,β'-dinitroanthraquinones with ammonia in water, ethers, aliphatic or cycloaliphatic or, aromatic hydrocarbons which may optionally be substituted by alkyl groups or, optionally, in mixtures of these compounds.

Accordingly, this invention relates to a process for the production of α-amino-β'-nitroanthraquinones, which is characterised by the fact that α,β'-dinitroanthraquinones and ammonia are reacted in ethers, aliphatic, cycloaliphatic or in aromatic hydrocarbons which may optionally be alkyl-substituted in water or in mixtures of these compounds, preferably under pressure, at elevated temperature, i.e., at a temperature of at least 100° C, preferably at a temperature in the range of from 100° to 220° C and, more particularly, at a temperature of from 140° to 200° C, the ammonia and α,β'-dinitroanthraquinone being reacted in a molar ratio of at least 3 : 1, more especially within the range of 10 : 1 to 40 : 1 and, more especially in a molar ratio in the range of from 15 : 1 to 30 : 1.

DESCRIPTION

It is possible to use both pure 1,6- and 1,7-dinitroanthraquinone, which may be obtained, for example, in accordance with Helv. Chim. acta 14, 1404, and also mixtures of these compounds.

Suitable ethers are, in particular, aliphatic, cycloaliphatic and aromatic ethers, such as dibenzylether, di-sec.-butylether, diisopentylether, ethyleneglycol dimethylether, diethyleneglycol dimethylether, diethyleneglycol diethylether, methoxycyclohexane, ethoxycyclohexane, dicyclohexylether, anisole, phenetol, diphenylether, 2-methoxynaphthalene, tetrahydrofuran, dioxan, amylphenylether, benzylisoamylether, dibenzylether, diglycol-di-n-butylether, glycolmethyleneether and methylbenzylether.

Suitable aliphatic and cycloaliphatic hydrocarbons are, for example, n-pentane, n-hexane, n-heptane, cyclohexane, methylcyclohexane, cyclododecane, decalin, cycloheptane, cyclopentane, n-decane, 1,2-dimethylcyclohexane, 1,3-dimethylcyclohexane, 1,4-dimethylcyclohexane, 2,2-dimethylpentane, 2,3-dimethylpentane, 2,4-dimethylpentane, 3,3-dimethylpentane, isopropylhexane, methylcyclohexane, 2-methylheptane, 3-methylheptane, 4-methylheptane, 2-methylhexane, 3-methylhexane, 2-methyloctane, 3-methyloctane, 4-methyloctane, 2-methylpentane, 3-methylpentane, n-octane, penta-isobutane, triethylmethane, 2,2,3-trimethylpentane, 2,2,4-trimethylpentane and 2,2,3-trimethylpentane.

Suitable aromatic hydrocarbons are, for example, benzene, toluene, o-, m-, p-xylene, isopropylbenzene, trimethylbenzene, diethylbenzene, tetramethylbenzene, diisopropylbenzene, isododecylbenzene, tetralin, naphthalene, methylnaphthalene diphenyl, diphenylmethane, o-, m-, p-cymol, dibenzyl, dihydronaphthalene, 2,2'-dimethyldiphenyl, 2,3'-dimethyldiphenyl, 2,4'-dimethyldiphenyl, 3,3'-dimethyldiphenyl, 1,2-dimethyl naphthalene, 1,4-dimethylnaphthalene, 1,6-dimethylnaphthalene, 1,7-dimethylnaphthalene, 1,1-diphenylethane, hexamethylbenzene, isoamylbenzene, pentamethylbenzene, 1,2,3,4-tetramethylbenzene, 1,2,3,5-tetramethylbenzene, 1,2,7-trimethylnaphthalene and 1,2,5-trimethylnaphthalene.

According to a preferred embodiment the process according to the invention is carried out under the following conditions: at a temperature of at least 100° C, preferably at a temperature in the range of from 100° to 220° C, and more especially at a temperature in the range of from 140° to 200° C and with a molar ratio (of ammonia to α,β'-dinitroanthraquinones) of at least 2 : 1, preferably in the range of 10 : 1 to 40 : 1 and more particularly in the range of 15 : 1 to 30 : 1. The reaction is generally carried out under superatmospheric pressure.

The reaction time is governed by the reaction temperature, the reaction pressure and the molar ratio, the reaction velocity increasing with increasing temperature and increasing molar ratio. For example, if the reaction is carried out at a pressure above 30 atms and with a molar ratio of 10 : 1 at a temperature of 200° C; 150° C; or 130° C, the reaction is completed after 0.5; 3; or 5 hours, respectively hours, whereas, for example, with a molar ratio of 50 : 1 and a reaction temperature of 100° C; or a ratio of 30 : 1 at 130° C or a ratio of 20 : 1 at 150° C, the reaction can be expected to take less than 5 hours; less than 4 hours or 0.5 hours respectively. The process can be carried out either continuously or in batches.

The reaction mixture can be worked up by conventional methods, for example by filtering off the product crystallised out of the organic solvent after cooling to room temperature. The mother liquor which accumulates can be recycled to the reaction. However, the reaction mixture can also be worked up by distilling off the solvent or by precipitating the α-amino-β'-nitroanthraquinones with the aid of a diluent which reduces the solubility of the α-amino-β'-nitroanthraquinones in the reaction solution (for example petroleum ether). If desired, the reaction product can be further purified by treatment with acids, for example sulphuric acid, or by distillation in vacuo. α-Amino-β-nitro-anthraquinones are dyes for synthetic fibres, or intermediate products for the production of these dyes which are obtained, for example, by acylating the amino group or by halogenation and/or optionally by other conversions of the kind known for α-amino-anthraquinones.

EXAMPLE 1

A mixture of 310 g of 1,6-dinitroanthraquinone (96%) and 1 liter of toluene was reacted with 170 g of ammonia in an autoclave for 2 hours at a temperature of 150° C (molar ratio 10 : 1; pressure 50 atms).

After cooling to room temperature, the reaction mixture was filtered under suction, the residue was washed with a little toluene and dried in vacuo. Yield: 277 g of a 93.1% 1-amino-6- nitroanthraquinone (96% of the theoretical yield).

Similar yields and purity levels can be obtained by using, instead of toluene, benzene, 1,3,5-trimethylbenzene, isopropyl benzene, isododecylbenzene, diphenylmethane, n-hexane, n-heptane, decalin, tetralin, methylcyclohexane, cyclododecane, n-dipropylether, dibutylether, diethyleneglycol dimethylether, diethyleneglycol diethylether, methoxycyclohexane, dicyclohexyl ether, anisole, phenetol, diphenylether, tetrahydrofuran, dioxan or mixtures thereof.

EXAMPLE 2

A mixture of 301 g of 1,7-dinitroanthraquinone (99%) and 1 liter of ethyleneglycol dimethylether was reacted with 510 g of ammonia in an autoclave over a period of 4 hours at a temperature of 130° C (molar ratio 30 : 1; pressure 60 atms). After cooling, the reaction mixture was poured into 5 litres of water and the deposit which precipitated was filtered off under suction, washed with water and dried. Yield: 264 g of a 93% 1-amino-7-nitroanthraquinone (91% of the theoretical yield).

EXAMPLE 3

310 g of 1,6-dinitroanthraquinone (96%) were reacted 0.5 hours with 340 g of ammonia (molar ratio 20:1; pressure 80 atms) in 1 litre of n-pentane in an autoclave at 150° C; the reaction mixture obtained was freed from the solvent by distillation. Residue: 269 g of a 91.5% 1-amino-6-nitroanthraquinone (89% of the theoretical yield).

EXAMPLE 4

A suspension of 317 g of 1,7-dinitroanthraquinone (94%) in 2 liters of water was stirred with 340 g of ammonia (molar ratio 20 : 1; pressure 40 atms) in an autoclave for a period of 2 hours at a temperature of 180° C. After venting, the reaction mixture was filtered under suction at room temperature. The mother liquor was recycled, whilst the residue was dried. Yield: 274 g of a 90% 1-amino-7-nitroanthraquinone (92% of the theoretical yield).

What is claimed is:

1. Process for preparing an α-amino-β'-nitroanthraquinone which comprises reacting an α,β'-dinitroanthraquinone with ammonia in an ether, an aliphatic, a cycloaliphatic or an optionally alkyl-substituted aromatic hydrocarbon, or a mixture of these.
2. Process of claim 1 wherein the reaction is carried out under superatmospheric pressure.
3. Process of claim 1 wherein the reaction is carried out in an alkylbenzene.
4. Process of claim 1 wherein the molar ratio of ammonia to α,β'-dinitroanthraquinones is at least 2 : 1.
5. Process of claim 4 wherein the molar ratio is in the range from 10 : 1 to 40 : 1.
6. Process of claim 5 wherein the molar ratio is in the range from 15 : 1 to 30 : 1.
7. Process of claim 1 wherein the reaction is carried out at a temperature of at least 100° C.
8. Process of claim 7 wherein the temperature is in the range of from 100° C to 200° C.
9. Process of claim 8 wherein the temperature is in the range of from 140° C to 200° C.
10. Process for preparing an α-amino-β'-nitroanthraquinone which comprises contacting an α,β'-dinitroanthraquinone with ammonia at a temperature of 140° to 200° C at a pressure above 30 atmospheres in an ether, an aliphatic, cycloaliphatic or an optionally alkyl-substituted aromatic hydrocarbon, water or a mixture thereof, the molar ratio of ammonia to α,β'-dinitroanthraquinone being in the range from 10:1 to 40:1.
11. A process according to claim 10 wherein reaction is performed in an ether, an aliphatic, a cycloaliphatic or an optionally alkyl-substituted aromatic hydrocarbon or a mixture thereof.

* * * * *